United States Patent [19]

Van Der Puy et al.

[11] Patent Number: 5,421,971
[45] Date of Patent: Jun. 6, 1995

[54] HYDROCHLOROFLUOROCARBONS AND HYDROFLUOROCARBONS AND METHODS FOR PRODUCING THE SAME

[75] Inventors: Michael Van Der Puy; Alagappan Thenappan, both of Cheektowaga; G. V. Bindu Madhavan, Amherst, all of N.Y.

[73] Assignee: AlliedSignal Inc., Morristown, N.J.

[21] Appl. No.: 116,935

[22] Filed: Sep. 3, 1993

[51] Int. Cl.$^6$ ............................................. C07B 39/00
[52] U.S. Cl. .............................. 204/157.6; 204/157.94; 204/157.95; 204/158.11
[58] Field of Search ........... 204/157.6, 157.94, 157.95, 204/158.11

[56] References Cited

U.S. PATENT DOCUMENTS

| | | | |
|---|---|---|---|
| 2,407,246 | 9/1946 | Benning et al. | 204/157.95 |
| 2,644,835 | 7/1953 | Ladd et al. | 260/465.7 |
| 4,947,881 | 8/1990 | Magid et al. | 134/40 |
| 5,059,729 | 10/1991 | Gervasutti | 570/175 |
| 5,120,883 | 6/1992 | Rao et al. | 570/123 |

FOREIGN PATENT DOCUMENTS

| | | |
|---|---|---|
| 123743 | 5/1991 | Japan . |
| 154734 | 5/1992 | Japan . |

OTHER PUBLICATIONS

83 Journal Amer. Chem. Soc. (Apr. 1961); "Cesium Fluoride Catalyzed Rearrangement of Perfluorodienes to Perfluorodialkylacetylenes", Miller et al. pp. 1767–1768.

Journal Americal Chem. Soc. (1959); "Oxidation of Polyhalogenocompounds. Part II. Photolysis and PhotoChemocal Oxidation of Some Chlorofluoroethanes", R. N. Haszeldine and F. Nyman, pp. 387–396.

Polyurethanes World Congress (1991–Sep. 24, 26, 1991); "1,1,1,4,4,4, Hexafluorobutane, a New Non–Ozone–Depleting Blowing Agent for Rigid PUR Foams", W. M. Lamberts, pp. 734–739.

Derwent Abstract No. 93-272768/34 of PCT Application No. 9316023 (published Aug. 19, 1993).

*Primary Examiner*—John Niebling
*Assistant Examiner*—C. Delacroix-Muirheid
*Attorney, Agent, or Firm*—Wayne W. Rupert; Jay P. Friedenson

[57] ABSTRACT

A process for the preparation of compounds of the formula, $F(CF_2)_aCCl_2CCl_2(CF_2)_bF$ where a and b are the same or different and are each an integer $\geq 1$ (including the novel compound $CF_3CF_2CCl_2CCl_2CF_2CF_3$), which comprises chlorination in the presence of irradiation, of at least one compound of the formula, $F(CF_2)_nCH_xCl_{3-x}$ where n is an integer $\geq 1$ and x is an integer $\leq 3$. There is also disclosed a process for utilizing the $F(CF_2)_aCCl_2CCl_2(CF_2)_bF$ compounds to produce $F(CF_2)_aCH_2CH_2(CF_2)_bF_3$ compounds which comprises contacting hydrogen and the $F(CF_2)_aCCl_2CCl_2(CF_2)_bF$ compounds in the presence of a catalysis which includes at least one Group VIII transition metal. A further aspect of the invention is a novel group of compounds, $F(CF_2)_aCCl_2CCl_2(CF_2)_bF$, wherein a and b are the same or different and are each an integer from 2 to 10, particularly 3,3,4,4-tetrachloroperfluorohexane (i.e., $CF_3CF_2CCl_2CCl_2CF_2CF_3$), whose corresponding hydrofluorocarbons can be used as cleaning solvents.

11 Claims, No Drawings

HYDROCHLOROFLUOROCARBONS AND HYDROFLUOROCARBONS AND METHODS FOR PRODUCING THE SAME

FIELD OF THE INVENTION

This invention relates to the novel synthesis of chlorofluorocarbons of the type $RfCCl_2CCl_2Rf$, where Rf is a perfluoroalkyl group, a novel group of compounds, $RfCCl_2CCl_2Rf$ which can be produced by this synthesis, and a novel reduction of chlorofluorocarbons of the type $RfCCl_2CCl_2Rf$ to the corresponding hydrofluorocarbons of the type $RfCH_2CH_2Rf$ and a novel use of the $RfCH_2CH_2Rf$ hydrofluorocarbons.

BACKGROUND OF THE INVENTION

Chlorofluorocarbons (CFCs) (i.e., compounds that contain only carbon, chlorine and fluorine atoms) are used in a variety of applications, although use of these materials is declining due to environmental regulations stemming from their role in the depletion of stratospheric ozone. Nonetheless, they remain useful chemical intermediates. In particular, they can function as precursors to hydrofluorocarbons (HFCs) (i.e., compounds that contain only hydrogen, fluorine and carbon atoms) and hydrochlorofluorocarbons (HCFCs) (i.e., compounds that contain only hydrogen, fluorine, chlorine and carbon atoms) which can be used in place of CFCs in many cases. HFCs are not believed to contribute to ozone depletion and HCFCs are believed to contribute less than CFCs to ozone depletion. Although useful HFCs and HCFCs have been found, the search continues for other useful HFCs and HCFCs (particularly those having at least four carbon atoms) and improved methods for making HFCs and HCFCs.

One area in which there has been limited exploration concerns compounds that have a —$CCl_2CCl_2$— radical. Compounds having a —$CCl_2CCl_2$— group are generally prepared by the chlorination of a suitable unsaturated material such as an alkyne or a vicinal dichloroalkene (e.g., —CCl=CCl—). For example, 2,2,3,3-tetrachloroperfluorobutane (i.e., $CF_3CCl_2CCl_2CF_3$) can be prepared by the chlorination of 2,3-dichloro-hexafluoro-2-butene (i.e., $CF_3CCl=CClCF_3$) or hexafluoro-2-butyne and 2,2,3,3-tetrachloroperfluoropentane (i.e., $CF_3CCl_2CCl_2CF_2CF_3$) can be prepared by the chlorination of $CF_3C\equiv CCF_2CF_3$ (see Miller et al., 83 *Journal Amer. Chem. Soc.* 1767 (1961)). Alternatively, depending on the remainder of the molecule, they may be prepared by chlorination of a saturated compound having a —$CH_2CH_2$— group. Such processes are of little utility when the —$CCl_2CCl_2$— compound is to be employed as the precursor to an HFC, since the reduction of its precursor (e.g. an alkyne) serves to provide the HFC. In other words, in order to obtain the desired HFC, the starting material for producing the —$CCl_2CCl_2$— compound must include the same number of carbon atoms as the desired HFC and the unsaturated bond must be in the correct position. A need exists, therefore, for an improved method of preparing CFCs containing a —$CCl_2CCl_2$— group, and for novel CFCs that contain a —$CCl_2CCl_2$— group which may be useful as intermediates for producing HFCs.

Alternative methods have been mentioned in the literature, but they do not appear practical primarily because of the low yields of the desired —$CCl_2CCl_2$— containing compound.

For example, U.S. Pat. No. 2,644,835 to U.S. Rubber describes a generic structure of $RCCl_2CCl_2R'$, wherein R and R' each contain a chain of at least two carbon atoms and R may be substituted with a list of radicals, fluorine being among them. Although fluorine is mentioned as a possible substituent, no CFCs are listed among the specifically identified compounds. The $RCCl_2CCl_2R'$ compounds were prepared by the reduction of reactants having a structure of $RCCl_3$ and $R'CCl_3$ in the presence of a catalyst, such as $PtO_2$, and a base, such as alcoholic ammonia.

Vapor phase thermal chlorination of $CF_3CH_xCl_{3-x}$ wherein x is 1 to 3 over a solid catalyst to give $CF_3CCl_3$ has recently been described, but no mention is made of products containing more than 2 carbons (see U.S. Pat. No. 5,120,883 to DuPont). In fact, the total of the reported two-carbon materials in the product mixture is nearly 100%. Similarly, the vapor phase chlorination of either $CF_3CF_2CH_3$ or $CF_3CF_2CH_2Cl$ gave three-carbon products totaling 100% of the product mixture (see Japanese Kokai Patent Publication No. 4-154734 to Asahi Glass).

Vapor phase photolysis of $CF_3CCl_3$ to $CF_3CCl_2CCl_2CF_3$ and chlorine has been reported (R. N. Haszeldine and F. Nyman, "Oxidation of Polyhalogeno-compounds. Part II. Photolysis and PhotoChemical Oxidation of Some Chlorofluoroethanes", *Journal Amer. Chem. Soc.*, 387-396 (1959)), but a conversion of 54% was obtained only after a period of 36 days.

A need also exists for an improved method of obtaining HFCs which are particularly useful as solvents. Japanese Kokai Patent Publication No. 3-123743 to Asahi Glass lists various HFCs, including $CF_3CF_2CH_2CH_2CF_2CF_3$, that are useful for degreasing and flux removal when used in a mixture that includes $CClF_2CF_2CHClF$ and/or $CF_3CF_2CHCl_2$ as a major component. Although $CF_3CF_2CH_2CH_2CF_2CF_3$ is mentioned in the examples, there is no description of a method for synthesizing this compound.

1,1,1,3,3,3,-Hexafluorobutane, the reduction product of $CF_3CCl_2CCl_2CF_3$, has been mentioned as a potential zero ODP blowing agent (W. M. Lamberts, Polyurethanes World Congress 1991, Sept. 24-26, 1991, p 734).

DESCRIPTION OF THE INVENTION

According to a first embodiment of the present invention, there is provided a process for the preparation of compounds of the formula, $F(CF_2)_aCCl_2CCl_2(CF_2)_bF$ where a and b are the same or different and are each an integer $\geq 1$, which comprises chlorination in the presence of irradiation, of at least one compound of the formula, $F(CF_2)_nCH_xCl_{3-x}$ where n is an integer $\geq 1$ and x is an integer $\leq 3$.

According to a second embodiment of the present invention, there is provided a novel group of compounds, $F(CF_2)_aCCl_2CCl_2(CF_2)_bF$, wherein a and b are the same or different and are each an integer from 2 to 10, particularly 3,3,4,4-tetrachloroperfluorohexane (i.e., $CF_3CF_2CCl_2CCl_2CF_2CF_3$).

According to a third embodiment of the present invention, there is provided a novel catalytic reduction of CFC compounds of the formula, $F(CF_2)_aCCl_2CCl_2(CF_2)_bF$ where a and b are the same or different and are each an integer $\geq 1$, to produce the corresponding HFC compounds of the formula, $F(CF_2)_aCH_2CH_2(CF_2)_bF$.

According to a fourth embodiment of the present invention, there is provided a method of cleaning contaminants from a surface of a substrate comprising treating said surface with a solvent composition comprising at least about 25 weight % of a compound represented by $F(CF_2)_aCH_2CH_2(CF_2)_bF$ based on the weight of the composition, wherein a and b are the same or different and are each an integer from 2 to 10.

As used herein, "irradiation" shall mean exposure to radiation of wavelengths shorter than those of visible light.

The CFCs produced by the first embodiment of the invention are represented by the formula $F(CF_2)_aCCl_2CCl_2(CF_2)_bF$ where a and b are the same or different and are each an integer $\geq 1$. If a and b are the same, it is evident that the CFC has a dimeric structure. Theoretically there is no upper limit on the value of the subscripts a and b, but if they are so large that the material is a solid, practice of the chlorination of the invention would not be practical. Preferably a and b can each be up to 10, more preferably up to 5. Preferably, a and b each range from 2 to 10, more preferably from 2 to 5, and most preferably a and b are each 2 providing the novel compound, 3,3,4,4-tetrachloroperfluorohexane, of the second embodiment of the invention. Illustrative of other CFCs produced by the chlorination of the invention are 2,2,3,3-tetrachloroperfluorobutane (i.e., $CF_3CCl_2CCl_2CF_3$), 2,2,3,3-tetrachloroperfluoropentane (i.e., $CF_3CCl_2CCl_2CF_2CF_3$), 2,2,3,3-tetrachloroperfluorohexane (i.e., $CF_3CCl_2CCl_2CF_2CF_2CF_3$), 3,3,4,4-tetrachloroperfluoroheptane (i.e., $CF_3CF_2CCl_2CCl_2CF_2CF_2CF_3$), and 4,4,5,5-tetrachloroperfluorooctane (i.e., $CF_3CF_2CF_2CCl_2CCl_2CF_2CF_2CF_3$). For the purposes of convenience, perfluoroalkyl groups will be represented herein by the designation "Rf". Such perfluoralkyl groups contain the same number of carbon atoms as described above for the subscripts a and b. The CFC products, therefore, can also be represented by $Rf_aCCl_2CCl_2Rf_b$.

The starting material or reactant can be any compound of the formula, $F(CF_2)_nCH_xCl_{3-x}$ where n is an integer $\geq 1$ and x is an integer $\leq 3$. Preferably, x is 1, 2 or 3. The starting material can also be represented by the formula $Rf_nCH_xCl_{3-x}$. Mixtures of $Rf_nCH_xCl_{3-x}$ compounds, as well as one single type of compound, can be used as reactants. Illustrative of suitable starting materials include 1,1-dichloro-2,2,3,3,3-pentafluoropropane (i.e., $CF_3CF_2CHCl_2$), 1-chloro-2,2,2-trifluoroethane (i.e., $CF_3CH_2Cl$), 1,1,1,2,2,3,3-heptafluorobutane (i.e., $CF_3CF_2CF_2CH_3$), and 1,1-dichloro-2,2,2-trifluoroethane (i.e., $CF_3CHCl_2$). These starting materials are commercially available from vendors, such as AlliedSignal ($CF_3CHCl_2$) or PCR Incorporated, or can be synthesized via conventional organic procedures. When the starting material contains 0 or only 1 chlorine atom, fully halogenated dimers will only appear after significant chlorine gas has been consumed.

The reaction, known in general as photochlorination, can be represented by the following equation:

$x + Cl_2 \rightarrow Rf_aCCl_2CCl_2Rf_b + Rf_nCCl_3 + HCl$

The desired products are those that contain the $—CCl_2CCl_2—$ radical. These products will be referred to herein as "dimeric" compounds because they all contain this dimeric radical, however, it should be recognized that the full structure of the compound may not be dimeric. For example, if only one type of organic starting material such as $CF_3CF_2CHCl_2$ is used, the only $—CCl_2CCl_2—$ containing compound produced will be $CF_3CF_2CCl_2CCl_2CF_2CF_3$, whose full structure is in fact dimeric. If a mixture of starting materials such as $CF_3CH_2Cl$ and $CF_3CF_2CHCl_2$ is employed, the $—CCl_2CCl_2—$ containing compounds produced will be $CF_3CCl_2CCl_2CF_3$, $CF_3CCl_2CCl_2CF_2CF_3$, and $CF_3CF_2CCl_2CCl_2CF_2CF_3$. It is evident that the full structure of the $C_4$ and $C_6$ compounds are dimeric but that the full structure of the $C_5$ compound is not dimeric.

If one type of organic starting compound is used, the only dimeric product typically produced is one that has double the number of carbon atoms of the starting compound. If a mixture of organic starting compounds is used, the resulting mixture of dimeric products could include a first dimeric product having double the number of carbon atoms of the starting compound having the smallest number of carbon atoms, a second dimeric product having double the number of carbon atoms of the starting compound having the largest number of carbon atoms, and products having the $—CCl_2CCl_2—$ radical and a number of carbon atoms ranging between those of the first and second dimeric products. It is important to recognize that the photochlorination of the invention allows for the production of CFCs that have at least twice the number of carbon atoms than the reactant having the smallest number of carbon atoms.

Reaction products that do not contain the $—CCl_2CCl_2—$ radical, such as $CF_3CF_2CCl_3$, will be referred to herein as "non-dimeric" compounds. In addition to monomeric products of the formula $Rf_nCCl_3$, the product mixture may also include partially chlorinated monomeric products of the formulas $Rf_nCH_yCl_{3-y}$ where y is 1 or 2, and $Rf_nCH_cCl_{2-c}CH_dCl_{2-d}$ where c and d are each 1 or 0, provided that c and d cannot both be 0.

The source of irradiation for the photochlorination is not critical and it may be provided by any conventional source such as sun lamps, Hg vapor lamps (high and low pressure) and bright incandescent lamps. Similarly, the type of reactor that may be used is not critical and could be an irradiation source surrounded by a cooling jacket that is immersed in the reactant mixture or the reactant mixture could be irradiated from a source located outside the vessel holding the reactant mixture. *Kirk-Othmer, Encyclopedia of Chemical Technology*, Vol. 17, pp. 545–554 (3d ed. 1982) contains a general description of the types of lights sources and reactors that may be used. On a laboratory scale there are a number of commercially available sun lamps or high intensity Hg lamps which are suitable.

Although any type of irradiation such as X-rays and gamma rays may be used, ultraviolet light is preferred. The wavelength should be about 2000 to about 14500 Å, preferably about 2200 to about 14000 Å.

The photochlorination is effected by contacting or admixing at least one of the previously described starting materials with chlorine gas in a reactor. Preferably, the starting materials are in the liquid phase and there is no solvent. If the starting materials are in the liquid phase as opposed to the vapor phase, the yield of desired dimeric product tends to increase substantially. Likewise, the presence of a solvent tends to be detrimental to the production of desired dimeric product.

The temperature of the reaction should initially be lower than the boiling point of the starting material and above the melting point of the starting material, so as to keep the starting material in the liquid phase. As the reaction proceeds, the boiling point of the reaction mixture increases, and the reaction temperature may be increased accordingly up to the boiling point. The reaction temperature of any individual photochlorination, therefore, will vary depending upon the boiling point of the starting material. In the case of $CF_3CHCl_2$, for example, the reaction temperature could vary from $-107°$ C. (melting point) to $27°$ C. (boiling point), although it is convenient to maintain the reaction temperature at about $0°$ C. to about $25°$ C. The yield of dimeric product, $Rf_aCCl_2CCl_2Rf_b$, appears to increase slightly with decreasing reaction temperature.

Preferably, substantially pure chlorine gas is fed into the reactor at such a rate that it is consumed as rapidly as it is added. The rate of consumption depends on the reactivity of the starting material, the temperature of the reaction, the light intensity and the reactor design. In general, chlorine feed rates, using a laboratory 450 watt medium pressure Hg lamp, are 30-110 cm$^3$/min (about 0.1 to 0.3 mol/h).

The chlorine feed rate tends to effect the percentage of dimeric product ($Rf_aCCl_2CCl_2Rf_b$) relative to non-dimeric product (e.g., $RfCCl_3$). In general, slower chlorine feed rates tend to enhance the percentage of dimeric product. Obviously, however, the rate of production of chlorinated species decreases as the chlorine feed rate is lowered. Thus, the optimum chlorine feed rate is a balance between throughput and the ratio of the desired dimeric product to non-dimeric products. The preferred chlorine feed rate is about 75 cm$^3$/min for reactions conducted at about $25°$ C. on a laboratory scale.

A convenient laboratory apparatus for performing the photochlorination is a glass reactor fitted with a water jacketed quartz immersion well into which the ultraviolet light lamp is placed. The glass reactor itself is also jacketed for the control of the reaction temperature by using a circulating fluid for heating or cooling.

As described above, the photochlorination reaction produces various non-dimeric products and HCl gas in addition to the desired dimeric product. The HCl gas can be removed from the product stream using conventional means such as absorption by a water or caustic scrubber or distillation. The non-dimeric products such as $RfCCl_3$ are themselves useful and can be separated from the dimeric product using conventional means such as distillation. The non-dimeric products then can be partially or completely reduced to $RfCH_xCl_{3-x}$ by conventional methods and then recycled back to act as a starting material for the photochlorination reaction. This reduction can be accomplished, for example, by conventional catalytic hydrogenation or photoreduction. The effluent from the reactor also includes unreacted chlorine gas which can be separated via conventional methods and recycled.

On a laboratory scale, effluent from the reactor, after passing through an optional condenser and cold trap (to collect the lower boiling organic materials such as the dimeric and non-dimeric products), includes HCl gas, which can be absorbed by a water or caustic scrubber, and unreacted chlorine. Preferably, chlorine is introduced by way of a sintered glass sparger, which is superior to an open tube with respect to a slight increase in the percentage of the desired dimeric product. When the reaction is deemed complete, as determined by the lack of chlorine consumption or by analysis, the crude product mixture is washed to remove dissolved HCl and chlorine and subsequently distilled to obtain pure product. The ratio of dimeric product ($Rf_aCCl_2CCl_2Rf_b$) to non-dimeric product ($RfCCl_3$) generally decreases with increasing conversion of the starting material. Thus, the percentage yield of dimeric product decreases with time, even though additional dimeric product is being formed throughout the reaction. Consequently, it is preferable to stop the reaction before the consumption of starting material is complete, at approximately 10% to 90% conversion, preferably at approximately 30% to 70% conversion, and most preferably at approximately 50% conversion.

As mentioned previously, the photochlorination process of the present invention provides a procedure for synthesizing a novel group of compounds, $F(CF_2)_aCCl_2CCl_2(CF_2)_bF$, wherein a and b are the same or different and are each an integer from 2 to 10, particularly $CF_3CF_2CCl_2CCl_2CF_2CF_3$. As explained below in more detail, these compounds are useful as intermediates for producing the corresponding HFCs which are useful in solvent cleaning applications. For example, $CF_3CF_2CCl_2CCl_2CF_2CF_3$ is an intermediate for producing $CF_3CF_2CH_2CH_2CF_2CF_3$.

In particular, $F(CF_2)_aCH_2CH_2(CF_2)_bF$) wherein a and b are the same or different and are each an integer from 2 to 10, compounds (especially $CF_3CF_2CH_2CH_2CF_2CF_3$) are useful as solvents for removing contaminants from the surface of a substrate. Additives such as rust inhibitors, surfactants, corrosion inhibitors, decomposition inhibitors, acid scavengers, antioxidants and emulsifiers may be added to the solvent in order to obtain additional desired properties. Moreover, $CF_3CF_2CH_2CH_2CF_2CF_3$ can be mixed with other components in order to enhance its practical use as a solvent. For example, about 5 weight % (based on the weight of the mixture) or more of a lower ($C_1-C_{10}$) alcohol, preferably at least a $C_2$ alcohol, can be mixed with the solvent in order to reduce its flammability. Any solvent mixture, however, should include at least about 25 weight %, preferably at least about 40 weight %, and most preferably at least about 75 weight % of the $F(CF_2)_aCH_2CH_2(CF_2)_bF$, based on the weight of the mixture. Of course, a solvent comprising substantially 100 weight % of the $F(CF_2)_aCH_2CH_2(CF_2)_bF$ compound also could be used.

The $F(CF_2)_aCH_2CH_2(CF_2)_bF$ compounds should remove most contaminants from the surface of a substrate. For example, $CF_3CF_2CH_2CH_2CF_2CF_3$ removes organic contaminants such as mineral oils. Under the term "mineral oils", both petroleum-based and petroleum-derived oils are included. Lubricants such as engine oil, machine oil, and cutting oil are examples of petroleum-derived oils. The solvents also may remove water from the surface of a substrate and it may be used in the single-stage or multi-stage drying of objects.

The surfaces of inorganic and organic substrates can be cleaned by the solvents. Examples of inorganic substrates include metallic substrates, ceramic substrates and glass substrates. Examples of organic substrates include polymeric substrates such as polycarbonate, polystyrene, and acrylonitrile-butadiene-styrene. Other substrates could be natural fabrics such as cotton, silk, fur, suede, leather, linen and wool and synthetic fabrics such as polyester, rayon, acrylics, nylon, and blends thereof. It should also be understood that composites of the foregoing materials may be cleaned by the solvents.

The solvent may be used in vapor degreasing, solvent cleaning, cold cleaning, dewatering, and dry cleaning. In these uses, the object to be cleaned is immersed in one or more stages in the liquid and/or vaporized solvent or is sprayed with the liquid solvent. Elevated temperatures, ultrasonic energy, and/or agitation may be used to intensify the cleaning effect.

Production of $CF_3CF_2CH_2CH_2CF_2CF_3$ from $CF_3CF_2CCl_2CCl_2CF_2CF_3$ can be achieved via a reduction reaction. The reduction of $F(CF_2)_aCCl_2CCl_2(CF_2)_bF$ (or $Rf_aCCl_2CCl_2Rf_b$) compounds to $F(CF_2)_aCH_2CH_2(CF_2)_bF$ (or $Rf_aCH_2CH_2Rf_b$) compounds can be achieved catalytically in the vapor phase. Such a reaction is advantageous due to the simplicity of the equipment and operation. The $Rf_aCCl_2CCl_2Rf_b$ to be reduced is passed, along with $H_2$ gas, over a catalyst bed consisting of a Group VIII transition metal or combinations thereof on an inert support. A mixture of $Rf_aCCl_2CCl_2Rf_b$ compounds, as well as a single $Rf_aCCl_2CCl_2Rf_b$ compound, can be passed over the catalyst. The $H_2$ feed gas can be substantially pure $H_2$ or it can be diluted with nitrogen in order to reduce the required contact time. In general, at least about 4 mol of $H_2$ should be reacted per 1 mol of each $Rf_aCCl_2CCl_2Rf_b$ compound and, preferably, about 8 to about 35 mol of $H_2$ per 1 mol of each $Rf_aCCl_2CCl_2Rf_b$ compound. By-products of the reaction are HCFCs which may be recycled to undergo further reduction which removes the remaining Cl atoms.

The active catalyst can be any transition metal, preferably a Group VIII transition metal. Particularly preferred are Ni, Pd and Pt, especially Pd. Such catalysts are well known and can be made by reducing the oxides or halides of the desired Group VIII transition metal. The support for the catalyst should be inert in the sense that it will not interfere with the reduction reaction. Well known catalyst supports that may be used include carbon and alumina (see U.S. Pat. Nos. 5,120,883 and 4,792,643, both incorporated herein by reference). The catalyst support may be washed with either water or acid. The alumina may assume a variety of forms—amorphous, crystalline, gel or solid. The catalyst support can have any structural shape, but typically it is in the form of a pellet, powder or granule upon which the active catalyst is coated, impregnated or dispersed. In the particular case of the reduction of $CF_3CF_2CCl_2CCl_2CF_2CF_3$, Pd coated on alumina pellets appears to be superior to Pd on carbon pellets with respect to conversion and purity of the crude product.

Temperatures of about 100° C. to about 300° C. can be used for the reduction, but temperatures in the range of about 150° C. to 210° C. are preferred. At these temperatures the catalysts are thermally stable and the reduction proceeds at an acceptable rate. Pressure is not critical. Atmospheric pressure can be used, but if higher pressures are used there is a tendency to improve the conversion to the corresponding HFC. The contact time with the catalyst should be about 0.1 to about 30 seconds, preferably about 5 to about 15 seconds.

It should be recognized that the photochlorination and the reduction according to the invention can be combined into a single process. Such a process allows one to start with the readily available $F(CF_2)_nCH_xCl_{3-x}$ compounds and derive a useful $F(CF_2)_aCH_2CH_2(CF_2)_bF$ compound. The combination would be effected by passing the dimeric products of the photochlorination mixed with $H_2$ over the reduction catalyst.

The present invention is illustrated more fully by the following non-limiting examples.

Example 1—Preparation of $CF_3CF_2CCl_2CCl_2CF_2CF_3$

The photolysis apparatus used in this Example 1 consisted of a glass reactor fitted with a water cooled, quartz immersion well for placement of a 450 watt medium pressure Hg lamp, and an inlet for the introduction of chlorine and an outlet for gaseous products. This apparatus is available from Ace Glass Co., Vineland, New Jersey. The reaction mixture was stirred magnetically. The outlet was connected to two cold traps, followed by a water scrubber.

The reactor was charged with 822 g (4.049 mol) of $CF_3CF_2CHCl_2$, prepared as outlined in U.S. Pat. No. 4,947,881, incorporated herein by reference. Chlorine gas was fed through the inlet tube at a rate of 75–80 mL/min with concomitant irradiation at a reaction temperature of 20°–24° C. After 7 hours, gas chromatography ("GC") analysis of the reaction mixture indicated that it was comprised of 43.0 area % starting material $CF_3CF_2CHCl_2$, 39.2 area % $CF_3CF_2CCl_3$, and 16.7 area % of a higher boiling material. The reaction mixture may also include dissolved chlorine and HCl, but the above percentages are based on the total organics of the reaction mixture. After a total of 15 h irradiation, the reaction mixture consisted of <0.1 area % starting material $CF_3CF_2CHCl_2$, 69.2 area % $CF_3CF_2CCl_3$, and 29.5 area % of the higher boiling material. The cold traps contained 36 g of starting material $CF_3CF_2CHCl_2$. The reaction mixture was washed twice with 250 mL 10% aqueous $NaHCO_3$ and twice with 200 mL water. After drying using $MgSO_4$, the reaction mixture was distilled to give 504.8 g $CF_3CF_2CCl_3$ (boiling point 74°–75° C. at 1 arm) and 188.3 g of the higher boiling product (boiling point 48°–50° C. at 5 mm Hg). The higher boiling product was identified as $CF_3CF_2CCl_2CCl_2CF_2CF_3$ based upon nuclear magnetic resonance and mass spectroscopy analysis. The yield, based on unrecovered $CF_3CF_2CHCl_2$, was 24%.

Example 2—Preparation of $CF_3CF_2CCl_2CCl_2CF_2CF_3$

Following the procedure described above in Example 1, 1400 g $CF_3CF_2CHCl_2$ was photochlorinated at 50° C. instead of 25° C. as in Example 1. The chlorine feed rate was 50 mL/min. The ratio of $CF_3CF_2CCl_3$ to $CF_3CF_2CCl_2CCl_2CF_2CF_3$ increased as the reaction progressed (from 3.6 after 12.5 h to 14.1 after 53.5 h when the reaction was complete). Work-up and distillation as described in Example 1 provided 159 g $CF_3CF_2CCl_2CCl_2CF_2CF_3$.

Example 3—Preparation of $CF_3CF_2CCl_2CCl_2CF_2CF_3$

The photoreactor of Example 1 was fitted with a condenser at −20° C. and charged with 1536 g $CF_3CF_2CHCl_2$. Chlorine gas was bubbled in subsurface using a sintered glass sparger. The reaction temperature was maintained at 30° C. during photolysis. After 21 hours, 100 g of $CF_3CF_2CHCl_2$ was recovered from the cold traps. The reaction mixture was washed 2 times with 150 mL 10% aqueous sodium bisulfite and dried using $Na_2SO_4$. Distillation gave 574 g of additional $CF_3CF_2CHCl_2$, 618 g $CF_3CF_2CCl_3$ (61% yield) and 300 g $CF_3CF_2CCl_2CCl_2CF_2CF_3$ (35% yield).

Example 4—Preparation of $CF_3CCl_2CCl_2CF_3$

Following the procedure described in Example 1, $CF_3CHCl_2$ (639 g) was photochlorinated over 18 h with a chlorine feed rate of 90 mL/min. Work-up and distillation as described in Example 1 provided 222 g $CF_3CCl_3$ (boiling point 46°-47° C.) and 140 g $CF_3CCl_2CCl_2CF_3$ (boiling point 134° C.). The latter is a known compound. The yield, based on unrecovered $CF_3CHCl_2$ (50 g unreacted $CF_3CHCl_2$ was found in the cold traps) was 24%.

Example 5—Preparation of $CF_3CCl_2CCl_2CF_3$

Following the procedure described in Example 3, 775 g $CF_3CHCl_2$ was photochlorinated using a chlorine feed rate of 30 mL/min. Periodically, samples were withdrawn and analyzed. The ratio of $CF_3CCl_3$ to $CF_3CCl_2CCl_2CF_3$ increased during the course of the reaction ($CF_3CCl_3/CF_3CCl_2CCl_2CF_3$ ratio (GC area %) was 1.8 after 9.75 h, 2.4 after 17.25 h, and 3.1 after 32.25 h when the reaction was complete). Distillation provided 105 g $CF_3CCl_2CCl_2CF_3$.

Example 6—Reduction of $CF_3CF_2CCl_2CCl_2CF_2CF_3$ to $CF_3CF_2CH_2CH_2CF_2CF_3$ The reactor in this Example consisted of a 1.25 inch diameter pyrex tube heated by means of electrical heating tape and an internal thermocouple to measure the temperature inside the tube. The reactor was packed with a mixture of 50 cm³ of 0.5% Pd/$Al_2O_3$ (⅛ inch pellets) and 100 cm³ of glass helices for a total bed volume of 150 cm³. The Pd/$Al_2O_3$ pellets are available from Aldrich Chemical or Engelhard Industries. Effluent from the reactor was condensed into cold traps maintained at −30° C. and −78° C. Hydrogen was passed into the tube at 155 mL/min, while $CF_3CF_2CCl_2CCl_2CF_2CF_3$ was metered into the top of the vertically mounted reactor at a rate of about 10 g/h. The temperature inside the reactor during the reduction was 202°–206° C. After a total reaction time of 3.75 h (38.1 g total $CF_3CF_2CCl_2CCl_2CF_2CF_3$ added), 20.15 g of product was collected in the cold traps, which was 99% pure according to GC analysis. The product was identified as $CF_3CF_2CH_2CH_2CF_2CF_3$ (boiling point 66° C., 80% yield) based on nuclear magnetic resonance and mass spectroscopy analysis.

Example 7—Chlorination of a mixture of $CF_3CHCl_2$ and $CF_3CF_2CHCl_2$

A mixture of 671 g $CF_3CF_2CHCl_2$ and 506 g $CF_3CHCl_2$ was photochlorinated at 30° C. (chlorine feed rate of 75 cm³/min) in a photochlorination apparatus equipped with a −15° C. condenser following the procedure described in Example 3. After 36 hours, the reaction was terminated. The cold traps contained 200 g of a 65:35 mixture of $CF_3CHCl_2$ and $CF_3CF_2CHCl_2$. The reaction mixture was washed three times with 75 mL water, dried using $Na_2SO_4$ and distilled to obtain pure $CF_3CCl_3$, $CF_3CF_2CCl_3$, $CF_3CCl_2CCl_2CF_3$, $CF_3CCl_2CCl_2CF_2CF_3$ (boiling point 151°–153° C.) and $CF_3CF_2CCl_2CCl_2CF_2CF_3$.

Example 8—Reduction of a mixture of $CF_3CCl_2CCl_2CF_3$, $CF_3CCl_2CCl_2CF_2CF_3$ and $CF_3CF_2CCl_2CCl_2CF_2CF_3$ A mixture of $CF_3CCl_2CCl_2CF_3$, $CF_3CF_2CCl_2CCl_2CF_3$, and $CF_3CF_2CCl_2CCl_2CF_2CF_3$ was hydrogenated at an average temperature of 220° C. and contact time of 20 seconds using a Pd/$Al_2O_3$ catalyst following the procedure described in Example 6. Analysis of the product mixture indicated the presence of $CF_3CH_2CH_2CF_3$, $CF_3CH_2CH_2CF_2CF_3$, and $CF_3CF_2CH_2CH_2CF_2CF_3$.

Example 9—Metal cleaning using $CF_3CF_2CH_2CH_2CF_2CF_3$

Cleaning studies were performed using metal coupons soiled with various oils. The weight of oil on the metal coupons was measured using an analytical balance. A test tube fitted with small cooling coils near the open end was used. A few mL of substantially pure $CF_3CF_2CH_2CH_2CF_2CF_3$ were added and brought to a boil. The cooling coils condensed the vapors. The soiled coupon was then placed in the test tube in the vapor zone, i.e., between the boiling liquid and the cooling coils. Three 10-second cleaning cycles were employed. The amount of oil remaining on the coupon was then determined. The results showed that this cleaning method removed substantial amounts of each type of oil. The amount of oil removed decreased in the order of—petroleum oil>semi-synthetic oil>synthetic oil.

We claim:

1. A process comprising irradiating chlorine gas and at least one compound having a structure represented by $F(CF_2)_nCH_xCl_{3-x}$, wherein n is an integer $\geq 1$ and x is an integer $\leq 3$ and said $F(CF_2)_nCH_xCl_{3-x}$ compound is in a liquid phase during said process, to produce a compound having a structure represented by $F(CF_2)_aCCl_2CCl_2(CF_2)_bF$, wherein a and b are the same or different and are each an integer $>1$.

2. A process according to claim 1, wherein said irradiating comprises irradiating with ultraviolet light.

3. A process according to claim 1, wherein said $F(CF_2)_nCH_xCl_{3-x}$ compound is selected from the group consisting of 1,1-dichloro-2,2,3,3,3-pentafluoropropane, 1-chloro-2,2,2-trifluoroethane, 1,1,1,2,2,3,3-heptafluorobutane, and 1,1-dichloro-2,2,2-trifluoroethane.

4. A process according to claim 1, wherein said $F(CF_2)_nCH_xCl_{3-x}$ compound has a boiling point, and the process further comprises maintaining said reactant mixture at a temperature below said boiling point.

5. A process according to claim 1, wherein a and b of said $F(CF_2)_aCCl_2CCl_2(CF_2)_bF$ compound are each independently from 2 to 10.

6. A process according to claim 1, wherein x of said $F(CF_2)_nCH_xCl_{3-x}$ compound is 1, 2 or 3, 7. A process according to claim 1, wherein only one said $F(CF_2)_nCH_xCl_{3-x}$ compound is subjected to said irradiation and a and b of said $F(CF_2)_aCCl_2CCl_2(CF_2)_bF$ compound are the same.

8. A process according to claim 1, wherein the reactant mixture does not include a solvent.

9. A process according to claim 1, further comprising reacting said $F(CF_2)_aCCl_2CCl_2(CF_2)_bF$ compound and hydrogen in the presence of a catalyst which includes at least one Group VIII transition metal to produce a compound having a structure represented by $F(CF_2)_aCH_2CH_2(CF_2)_bF$, wherein a and b are the same as in said $F(CF_2)_aCCl_2CCl_2(CF_2)_bF$ compound.

10. A process according to claim 1, wherein there are more than one of said $F(CF_2)_nCH_xCl_{3-x}$ compound and n, x, a and b are selected so that the number of carbon atoms in said $F(CF_2)_aCCl_2CCl_2(CF_2)_bF$ compound is at least double the number of carbon atoms in said $F(CF_2)_nCH_xCl_{3-x}$ compound having the least number of carbon atoms.

11. A process according to claim 1, wherein there is one said $F(CF_2)_nCH_xCl_{3-x}$ compound and n, x, a and b are selected so that the number of carbon atoms in said $F(CF_2)_aCCl_2CCl_2(CF_2)_bF$ compound is double the number of carbon atoms in said $F(CF_2)_nCH_xCl_{3-x}$ compound.

* * * * *

UNITED STATES PATENT AND TRADEMARK OFFICE
CERTIFICATE OF CORRECTION

PATENT NO. : 5,421,971
DATED : June 6, 1995
INVENTOR(S) : Van Der Puy et al.

It is certified that error appears in the above-identified patent and that said Letters Patent is hereby corrected as shown below:

Column 10:
  Claim 1, line 35, "integer > 1" should read --integer ≥ 1--.

Signed and Sealed this

Twelfth Day of December, 1995

Attest:

BRUCE LEHMAN

*Attesting Officer*   *Commissioner of Patents and Trademarks*